United States Patent
Wolfrum et al.

(10) Patent No.: US 6,849,402 B1
(45) Date of Patent: Feb. 1, 2005

(54) METHOD AND DEVICE TO QUANTIFY DNA AND RNA

(76) Inventors: Jürgen Wolfrum, Südring 2, D-37124 Rosdorf (DE); Markus Sauer, Odenwaldstrasse 48 II, D-69124 Heidelberg (DE); Kyung-Tae Han, Löwensteinerstrasse 107, D-71543 Wüstenrot (DE)

(*) Notice: Subject to any disclaimer, the term of this patent is extended or adjusted under 35 U.S.C. 154(b) by 0 days.

(21) Appl. No.: 09/669,236

(22) Filed: Sep. 25, 2000

(30) Foreign Application Priority Data

Apr. 1, 1998 (DE) .......................................... 198 14 682

(51) Int. Cl.[7] .................. C12Q 1/68; C12P 19/34; C12M 1/34; C07H 21/02; C07H 21/04
(52) U.S. Cl. .................. 435/6; 435/7.1; 435/91.1; 435/91.2; 435/283.1; 435/285.1; 435/287.2; 250/216; 536/22.1; 536/23.1; 536/24.3; 536/24.31; 536/24.32; 536/24.33; 536/24.34
(58) Field of Search .................. 435/6, 7.1, 91.1, 435/91.2, 287.2, 285.1, 283.1; 250/216

(56) References Cited

U.S. PATENT DOCUMENTS

| | | | | |
|---|---|---|---|---|
| 5,567,627 A | * | 10/1996 | Lehnen | 436/518 |
| 5,670,316 A | * | 9/1997 | Sena et al. | 435/6 |
| 5,756,297 A | * | 5/1998 | Fujiwake | |
| 6,121,603 A | * | 9/2000 | Hang et al. | 250/216 |
| 6,171,785 B1 | * | 1/2001 | Higuchi | 435/6 |

FOREIGN PATENT DOCUMENTS

| | | | |
|---|---|---|---|
| EP | 0798388 A1 | * | 1/1997 |
| EP | 0819769 A2 | | 1/1998 |
| GB | 2273772 A | | 6/1994 |
| JP | 410117797 A | * | 5/1998 |
| WO | WO 9508646 | | 3/1995 |

* cited by examiner

Primary Examiner—Jeffrey Siew
(74) Attorney, Agent, or Firm—Henry M. Feiereisen; Ursula B. Day (57) ABSTRACT

The invention relates to a device and a method for the detection, especially on line detection, of an amplification of a DNA and/or RNA sequence in a sample. The amplification of the DNA and/or RNA sequence in the sample is evaluated on the basis of scattered-light signal of the sample.

5 Claims, 7 Drawing Sheets

METHOD AND DEVICE TO QUANTIFY DNA AND RNA

CROSS-REFERENCES TO RELATED APPLICATIONS

This application claims the priority of German Patent Application, Serial No. 198 14 682.5, filed Apr. 1, 1998, pursuant to 35 U.S.C. 119(a)-(d), the disclosure of which is incorporated herein by reference.

This application is a continuation of prior filed copending PCT International application no. PCT/EP99/02242, filed Apr. 1, 1999, which designated the United States and on which priority is claimed under 35 U.S.C. §120, the disclosure of which is hereby incorporated by reference.

The invention concerns a device and a method to quantify DNA and RNA sequences. In particular, the invention concerns a method and a device to detect the amplification of a DNA and/or RNA sequence in a sample, especially the online detection of the amplification of a DNA and/or RNA sequence in a sample.

The detection of special DNA and RNA sequences in a sample by adding a complementary DNA or RNA sequence to the sample is a common diagnostic method. To evaluate the result, the amplification process must be observable or detectable. This is preferably done by quantifying the amplification process.

In the ABI TaqMan method, fluorescent energy transfer is used. The TaqMan probe (an oligonucleotide that hybridizes on the template on the location up to which the template is built during the PCR reaction) is marked at the 5 or 3-end of the oligonucleotide with a donor or acceptor dye. However, only the acceptor fluorescence is detectable since the donor fluorescence is quenched by the energy transfer to the acceptor. After the template has been successfully synthesized during the PCR reaction, the 5-terminal base of the TaqMan probe is digested. The close, fixed contact with the acceptor dye is lost, and the fluorescence signal rises. For reference, a free dye that emits at a different wavelength is added to the solution.

A disadvantage of this method is that adding the fluorescent dye required for measurement contaminates the sample. The sample cannot be directly processed further. The required purification steps may render the sample useless if the purification is unsuccessful.

The problem of the present invention is therefore to present a method and device to quantify DNA and RNA sequences that are easier and more efficient than the state-of-the-art methods and devices.

This problem is solved by the method and device in the independent claims. Other advantageous developments are presented in the dependent claims.

In particular, the problem is solved by a method for online detection of the amplification of a DNA and/or RNA sequence in a sample where the amplification of the DNA and/or RNA sequence in the sample is evaluated using the scattered light signal of the sample. It was surprisingly found that the amplification of DNA or RNA can be detected online without additives. The scattered light signal of the RNA or DNA molecules is used for this purpose. The method according to the invention is based on the fact that the intensity of the Rayleigh scatter (particle size $\ll \lambda$, wavelength of light) is proportional to the light intensity $I_0$, molecule size $M_c$, and the concentration of the particles.

$$I \sim I_0 M_c c$$

By exploiting the scattered light signal, it is no longer necessary to use fluorescent dyes such as FAM, JOE, TAMRA and ROX. By continually measuring the scattered light signal, the amplification can be quantitatively determined.

In another preferred method according to the invention, the sample is excited by a source which can be a light source, preferably a lamp, laser, or light-emitting diode. A xenon lamp or a helium-neon laser is particularly preferred. In this preferred embodiment of the present invention, sources with a wide range of emission spectra can be used by obtaining information from the scattered light signal. It is therefore not necessary as in the state of the art to use a special laser light source.

In another preferred exemplary embodiment of the present invention, a method is used in which the scattered light signal corresponds to the scattered light intensity. Such a correspondence can be recorded with a detector, especially a pin diode, to quantitatively determine the amplification.

The method according to the invention has several advantages due to its simplicity. No primer or nucleotide has to be marked, and the sample can be used directly afterwards without purification steps. The reaction can be detected online by the scattered light intensity and hence provides a more reliable, simple and cost-effective option for detecting amplification. It is also preferable to test the amplification by determining starting and end points.

In another preferred method of the present invention, the sample contains impurities, especially foreign DNA and/or RNA sequences. Added mononucleotides prevent the amplification from being followed while measuring absorption; however, it was surprisingly found that the added mononucleotides do not interfere with the measurement of scattered light. Another advantage of the present invention is hence that the method according to the invention allows detection of the amplification of a desired DNA and/or RNA sequence in a sample even when foreign DNA, RNA, and/or proteins are present since only the increase in scattered light intensity is measured. In the online detection of amplification, the viscosity (for example) and/or other properties of the solution can hence change without influencing the method according to the invention. It is particularly preferable to use the method for detection, especially online detection, when amplifying a DNA and/or RNA sequence in a a- contaminated sample. Self-measurements are therefore possible of DNA or RNA samples with excess foreign DNA or RNA taken from cell cultures.

In another preferred exemplary embodiment of the present invention, a method is provided whereby the products and/or educts are quantitatively measured for known initial or final concentrations of products and/or educts. In addition to a non-selective qualitative determination of whether amplification has occurred, the method according to the invention allows quantitative measurement of the products or educts. Real-time detection (online) is preferable. The initial or end concentrations of the products/educts are preferably taken into consideration for this determination.

The method according to the invention can be used for temperature cycling amplification (polymerase chain reaction PCR (RT PCR), ligase chain reaction LCR, transcription-based amplification) as well as isothermal amplification (strand displacement amplification, nucleic acid sequence based amplification NASBA, Qβ-replicase systems) and other amplification reactions.

The problem is also solved by a device to quantify the amplification of a DNA and/or RNA sequence in a sample that has the following components: A device to excite the sample, and a detection device. The detector can detect a scattered light signal from the sample. It was surprisingly found that this device to measure scattered light can determine the amplification of the DNA and/or RNA sequence in a sample.

In another advantageous exemplary embodiment of the present invention, the excitation device is a light source, preferably a lamp, laser or especially a LED. In this preferred embodiment of the present invention, the sources can use a wide range of emission spectra since the information is obtained from the scattered light source. It is therefore not necessary to use a laser light source with a special frequency range as in the state of the art.

Another preferred embodiment is distinguished in that the detector is a photomultiplier (PMT) and/or a CCD camera and/or a diode, and especially an avalanche photodiode (APD) and/or at least one PIN diode (16). The scattered light signal can be detected with a photomultiplier and/or a CCD camera and/or a diode. It is preferable to use a combination of differently wired PIN diodes so that the special measuring situation of the individual detectors can be taken into consideration. It is accordingly possible to preferably detect scattered light signals of predetermined frequency ranges by using filters. It is also possible to detect the signals of different PIN diodes and combine the different signals to define the end signal. It is also conceivable to use an imaging device for the detector, preferably a CCD camera. A PMT and/or ADP are preferably used if small amounts of substances are to be detected since they are very sensitive.

Another preferred device of the present invention has a scanner. A scanner can be used to transmit a special scattered light signals from the sample to the detector. In this preferred exemplary embodiment of the invention, specific scattered light signals of the special sample can be transmitted to a special detector.

In another preferred device of the invention, several sample carriers, preferably microtiter plates or capillaries are used. This makes it possible to observe and preferably scan several samples in one step. This increases the efficiency of the observation and detection methods. In addition, series of samples can be observed simultaneously, and associated measurements can be processed together.

Another preferred device according to the invention has sample carriers that can be scanned with the scanner. This makes it possible to scan the sample carrier e.g. in the x-y direction. The samples in the sample carriers are preferably in a plane and are scanned and measured sequentially. It is also possible for the sample carriers to be designed to be mobile; they can be moved so that the scanner can examine one sample after the other. In addition, it is preferable for both the sample carrier and the scanner to be mobile so that the sample carriers can be exchanged and the scanner can be swung to optimally exploit the setup and loading time for the device according to the invention. The fixed sample carrier is scanned by the moving scanner, and then the scanner is moved to another field of sample carriers while the first sample carriers are processed further or exchanged.

Another preferred device according to the invention has a scanner with a preferably moving mirror that can direct a scanning beam of the scanner. This makes it possible to fix the scanner so that it and the sample carriers do not have to be moved. In this preferred exemplary embodiment, only the mirror is moved to transfer to the detector the corresponding scattered light signals of the individual samples in the sample carriers. It is preferable for the sample carriers to be scanned (especially cyclically) in a set sequence to more-or-less continuously detect the scattered light signal of each sample using the known position of the mirror. For example, at time t1, a sample carrier P1 can be detected, at time t1+T sample carrier P2 can be detected, etc. up to time t1+NT where sample carrier P1 is redetected (N is the number of sample carriers P to be detected, and T is the time to measure and detect the following sample). For special sample x in sample carrier Px, the detection of the scattered light signals and hence the process of amplifying a DNA and/or RNA sequence in sample x is hence more-or-less continuous by interpolating the measured values of sample x at times:

$$tx, tx+NT, tx+2NT, \ldots tx+iNT, \text{etc.}$$

Another preferred embodiment of the present invention concerns a device where the excitation mechanism is designed so that the sample carriers or samples can be excited over a wide area, and the scattered light signals corresponding to the individual sample carriers can be individually detected by the detector. This makes it possible to simultaneously detect and evaluate a large-area sample or sample fields or sample carriers distributed over a large area. Continuous, diffuse excitation of the sample field is sufficient since the relative scattered light intensity that is independent of the absolute scattered light signal at each site is detected independently for each sample or section of the sample field.

In another preferred embodiment of the present invention, the device has a detecting device with at least two individual detectors that detect different scattered light signals. This makes it possible for several samples to be detected simultaneously and not sequentially. This is particularly advantageous when a precise simultaneous evaluation of the samples is desirable. It is particularly preferable to connect the individual detectors via optical fibers to the sample carriers or samples so that the profiles of the sample fields can also be detected using an optical fiber bundle. It is also preferable to record a large-area sample field with a CCD camera and detect the scattered light signals at the individual sites by evaluating the picture, preferably with a controller and especially preferably via a computer or image processing system.

It is also preferable to provide a controller to which signals are sent that correspond to the detected scattered light signals, and the controller evaluates the signals. This controller can process the individual measured values in the corresponding matrices for the individual samples and send them to a memory. In addition, a scanner can also be controlled by the controller, and the detectors can be set e.g. in regard to their sensitivity and alignment toward the samples.

In an additional advantageous use of the present, invention, the device to measure scattered light can quantify the amplification of a DNA and/or RNA sequence in a sample.

In the following, other advantageous embodiments of the invention will be explained with reference to the drawing. Shown are.

Figure 1A:
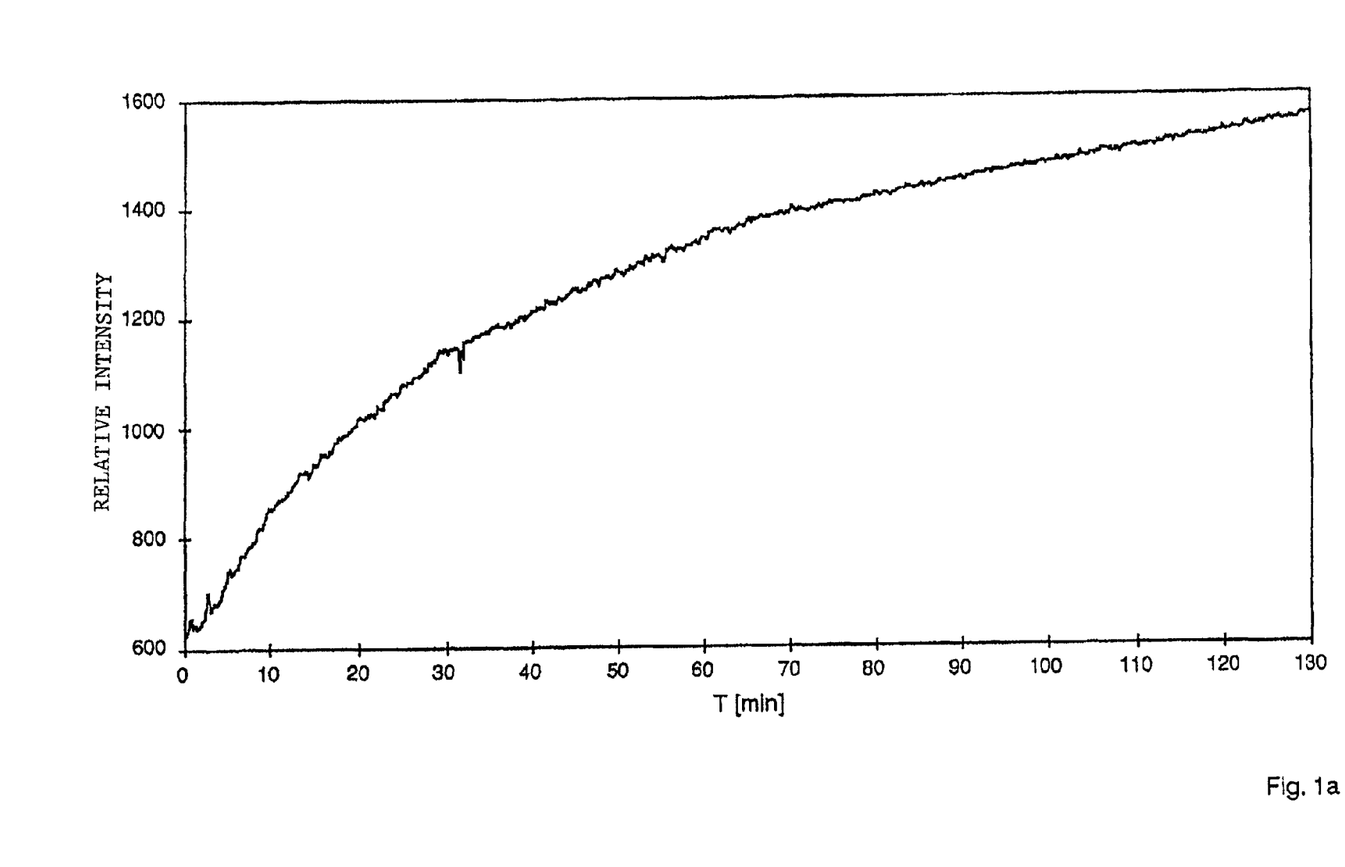
FIG. 1A A graph of the scattered light intensity measurement at a given concentration according to an exemplary embodiment of the method according to the invention.

FIG. 1a shows a graph of a scattered light intensity measurement of an exemplary embodiment of a method according to the invention at a given concentration. One can clearly see the rise in the relative scattered light intensity over time. This curve represents the advancing amplification in the sample.

Figure 1B:
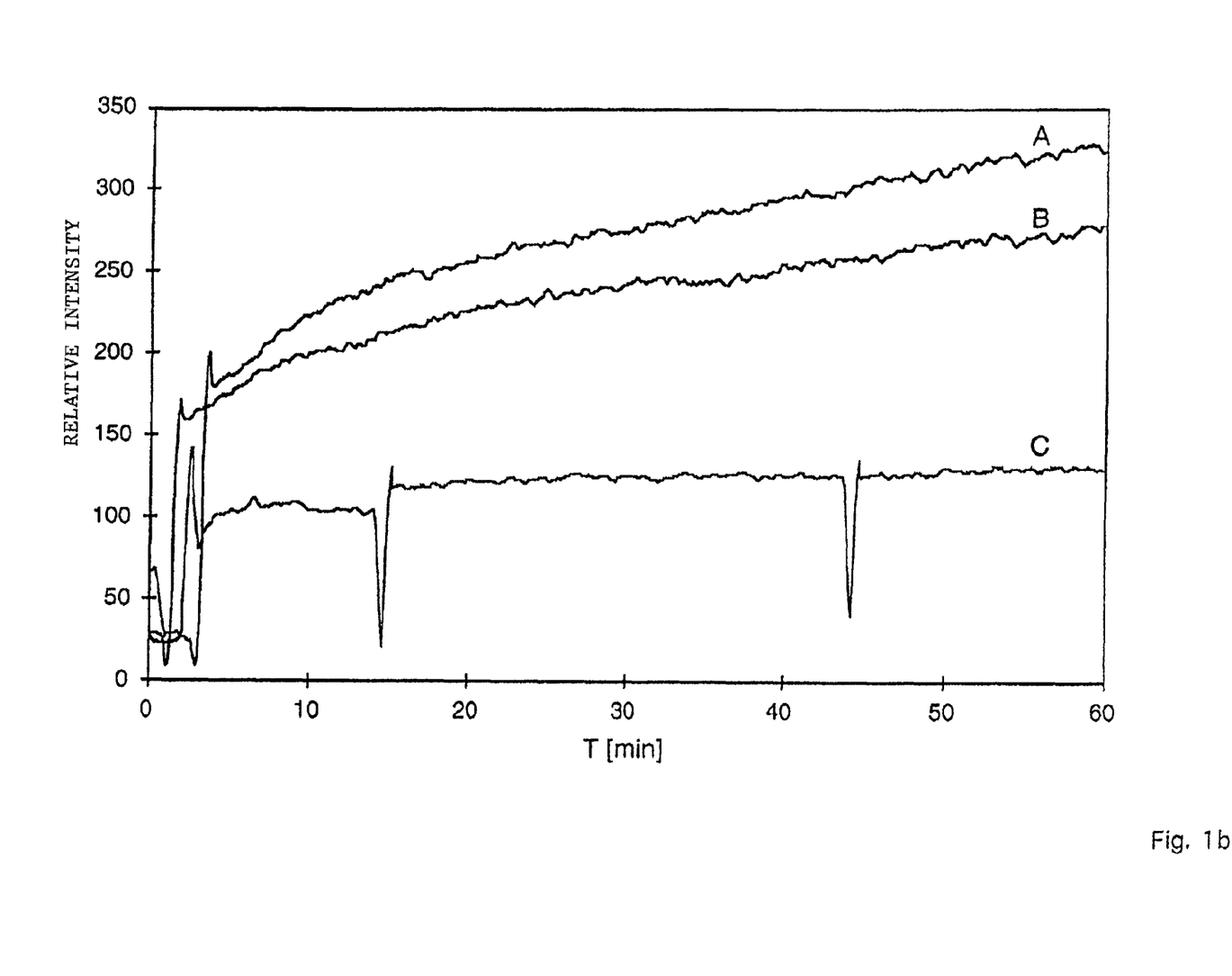
FIG. 1B A graph of the scattered light intensity measurement according to FIG. 1A at two diluted concentrations (curves A and B) together with a negative control (curve C).

FIG. 1b is a graph of a scattered light intensity measurement according to the exemplary embodiment of a method according to the invention from FIG. 1 at two diluted concentrations (curves A and B). In addition, the curve of a negative control (curve C) is also shown. This illustrates that one can also evaluate the quality by measuring the relative scattered light intensity. In the case of the negative control (curve C), there is no rise in the relative scattered light intensity. At the start of measurement, enzymes were added for A and B that triggered the amplification. No mononucleotide triphosphate was added to the negative control.

Both FIG. 1a and 1b concern AmpliScribe™ SP6 reactions (Epicentre Technologies)—a commercially available amplification of RNA by transcription—at a reaction temperature of 39° C.

| Components | Volume Curve A/B/C | Final Concentration | | |
|---|---|---|---|---|
| | | Curve A | Curve B | Curve C |
| ATP (100 mM) | 2/2/0 µl | 2.8 mM | 2.3 mM | 0 mM |
| CTP (100 mM) | 2/2/0 µl | 2.8 mM | 2.3 mM | 0 mM |
| GTP (100 mM) | 2/2/0 µl | 2.8 mM | 2.3 mM | 0 mM |
| UTP (100 mM) | 2/2/0 µl | 2.8 mM | 2.3 mM | 0 mM |
| DTT (100 mM) | 4 µl | 5.6 mM | 4.6 mM | 5 mM |
| AmpliScribe SP6 enzyme solution | 4 µl | | | |
| Water | 47/63/63 µl | | | |
| 10× SP6 reaction buffer | 7 µl | 1× | 0.8× | 0.9× |
| DNA control template (0.5 µg/µl) | 1 µl | 1 µg | 1 µg | 1 µg |
| Total volume | 72/88/89 µl | | | |

Figure 2A:
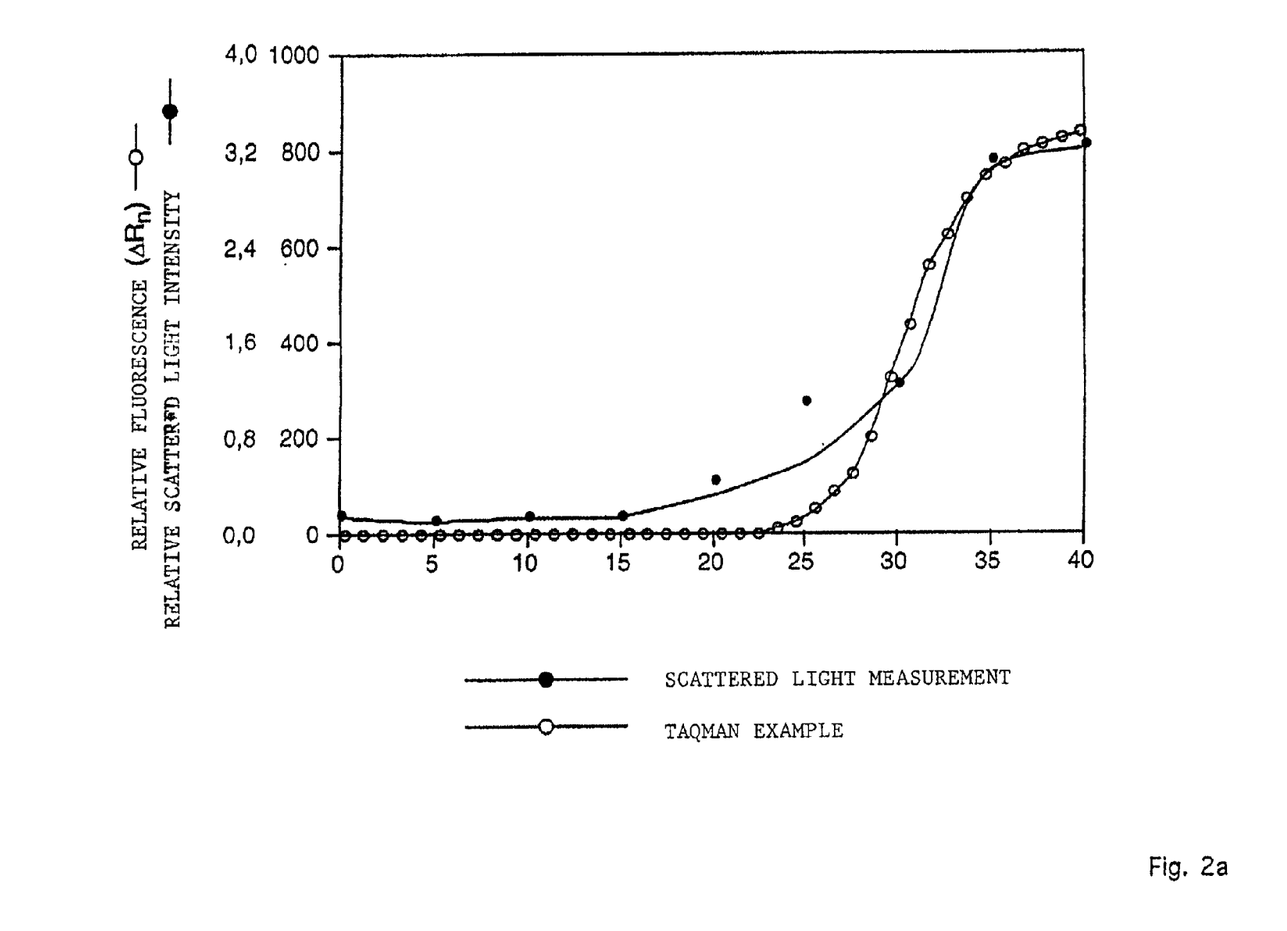
FIG. 2A A graph showing a comparison of the fluorescence measurement using the prior art TaqMan method and the scattered light measurement according to the method of the invention.

FIG. 2a shows a graph that that compares the measurement of fluorescence according to the state-of-the-art and the measurement of scattered light according to the invention. The measuring points of the scattered light measurement are shown as black dots while the fluorescence measurements are shown as circles. One can easily see that amplification can be demonstrated by both measurements.

Below are the test conditions for measuring scattered light according to the invention:

| Components | Vol./reaction | Final conc./reaction |
|---|---|---|
| ATP (10 mM) | 1 µl | 200 µM |
| CTP (10 mM) | 1 µl | 200 µM |
| GTP (10 mM) | 1 µl | 200 µM |
| TP (10 mM) | 1 µl | 200 µM |
| Primer A | Variable | 0.1 µM |
| Primer B | Variable | 0.1 µM |
| AqDNA polymerase | 0.5 µl | 2.5 U |

-continued

| Components | Vol./reaction | | Final conc./reaction |
|---|---|---|---|
| (5U/µl) | | | |
| Water | Variable | | |
| 10× PCR buffer | 5 µl | | 1× |
| DNA template | Variable | | Ca 0.25 µg/reaction |
| Total volume | 50 µl | | |
| Cycling conditions: | 92° C. | 120 s | |
| | 95° C. | 20 s | |
| | 60° C. | 30 s | |
| | 72 ° C. | 60 s | 40× cycles |

After five cycles in each case, a sample is removed and diluted at the end of the 72° C. step for the scattered light measurement and diluted with 50 µl water.

Figure 2B:
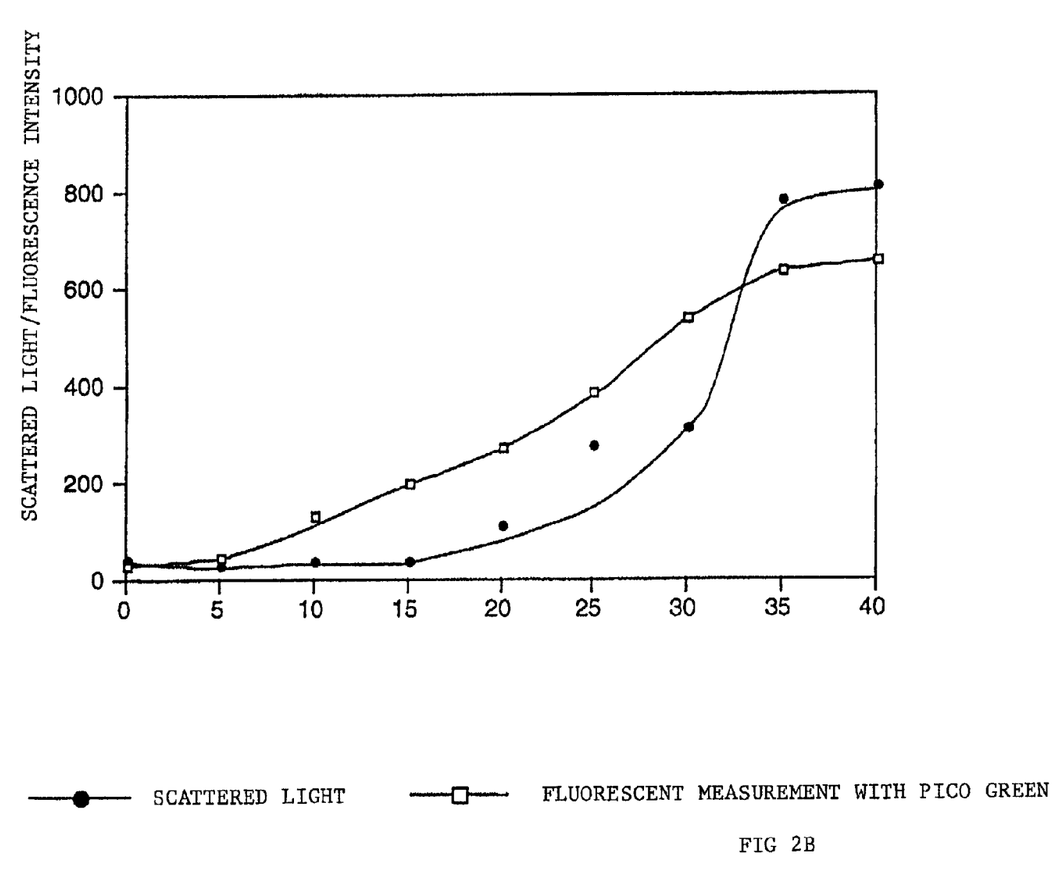
FIG. 2B A graph showing a comparison of the fluorescence measurement using a prior art intercalation dye and the scattered light measurement according to the method of the invention.

FIG. 2b shows a graph that compares the measurement of a fluorescence using state-of-the-art intercalation dye and a measurement of scattered light according to the invention. This comparative measurement was done with intercalating agent PicoGreen:

The same samples were used here that were used to measure scattered light intensity in FIG. 2a but only with 2 µl of the reaction solution diluted with 60 µl water and 20 µl PicoGreen (1:20 dilution) solution. The samples were excited at 480 nm, and the amplification was detected at 525 nm. One can clearly see that the success of the PCR reaction has been demonstrated in this case as well.

Figure 3:
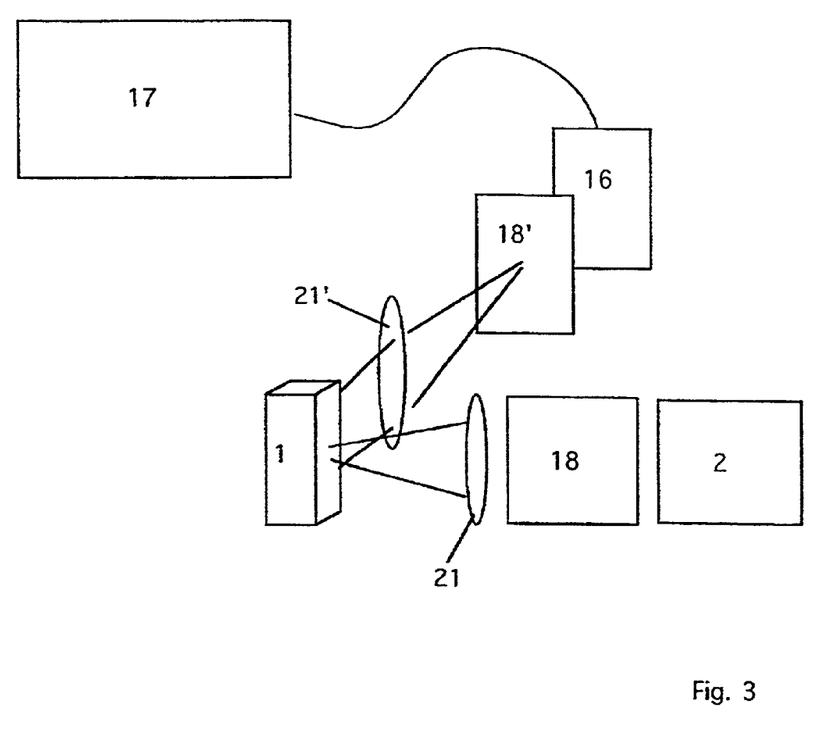
FIG. 3 A schematic design of an exemplary embodiment of the device according to the invention with a sample.

FIG. 3 shows a schematic diagram of an exemplary embodiment of the device according to the invention with a sample. Sample 1 is excited by a light source 2. The light emitted by the source is guided by monochromators 18 and focused by a lens 21 on the sample. The scattered light is transferred by lens 21' via monochromator 18' to PIN diode 16 that is used as a detector. A controller 17 that evaluates and records the signals is connected to the detector.

Figure 4:
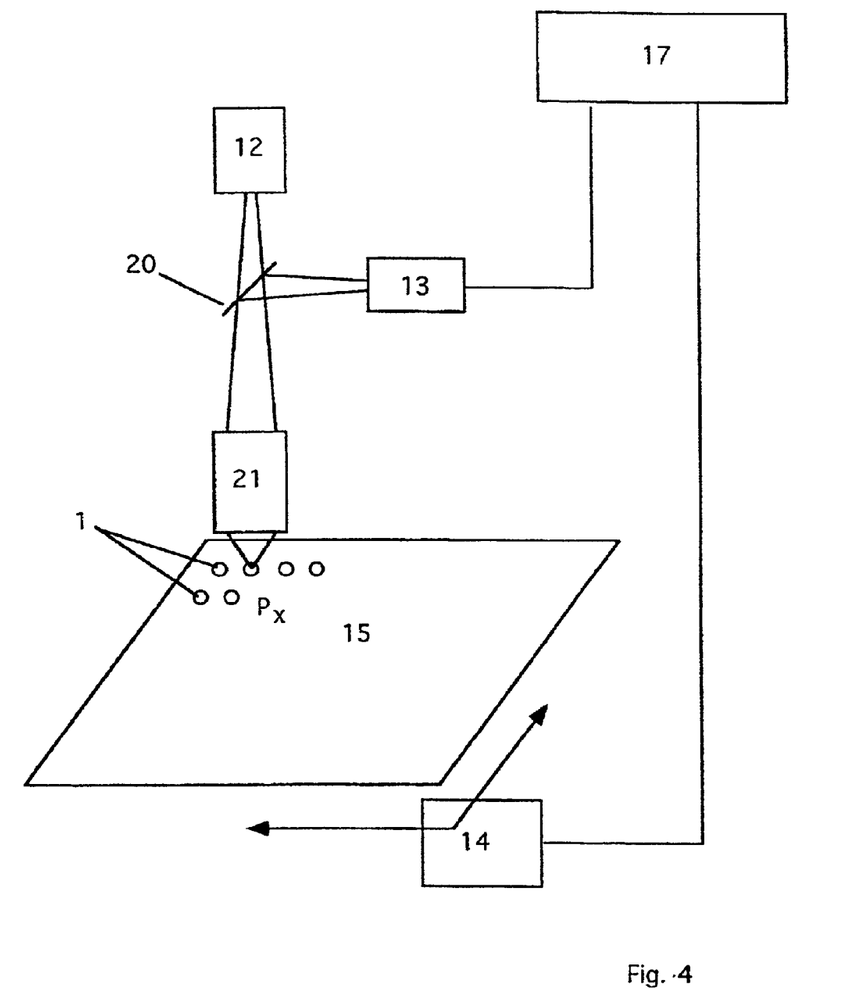
FIG. 4 A schematic design of an exemplary embodiment of the device according to the invention with numerous samples or sample carriers and a scanner.

FIG. 4 shows a schematic diagram of an exemplary embodiment of the device according to the invention with numerous samples 1 or sample carriers 15 and a scanner. Sample carriers 15 are arranged in a sample field 1. An exciter (excitation laser in this case) emits light and excites a sample Px via a lens or microscope objective 21. The scattered light is transferred via lens 21 and glass pane 4 to the detector 13. The detector is connected to a controller 17. This controller controls a scanner 14 that can move the sample field 1.

The controller sends a control pulse to the scanner and causes it to move a special sample into the focus of the lens 21. Then a measurement is made, the measured value is detected and saved, and then the scanner is controlled by another control signal from the controller that moves the next sample into the focus of the lens 21, and the sample is measured. The samples can accordingly be cyclically recorded and measured preferably in a cyclical manner.

Figure 5:
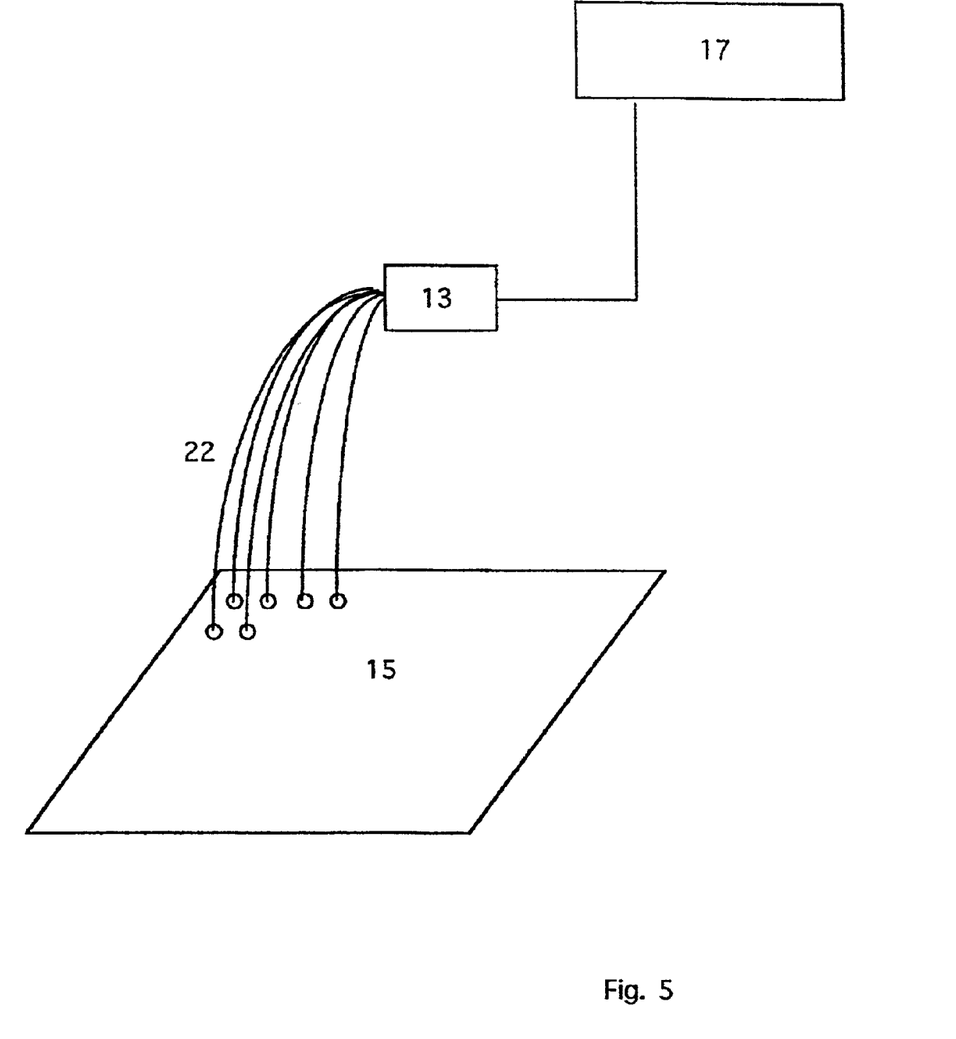
FIG. 5 A schematic design of an exemplary embodiment of the device according to the invention with numerous samples or sample carriers and optical fibers.

FIG. 5 shows a schematic diagram of an exemplary embodiment of the device according to the invention with numerous samples or sample carriers and optical fibers. The detector 13 is connected via optical fibers 22 to the sample 1. The excitation light is transmitted via the optical fibers, and the scattered light is also detected via the optical fibers. The detector sends the detected signals to the controller (17) where they are processed and buffered as needed.

A device and method have been presented for the detection (especially the online detection) of the amplification of a DNA and/or RNA sequence in a sample. The amplification of the DNA and/or RNA sequence in the sample is based on the scattered light signal of the sample. This method and device to quantify DNA and RNA sequences are easier and more efficient to use online than state-of-the-art methods and devices.

Reference Number List

1 Sample
2 Source, especially a light source
12 Excitation device
13 Detector
14 Scanner
15 Sample carrier
16 PIN diode
17 Controller
18 Monochromator
19 Mirror
20 Glass plate
21 Lens
22 Optical fibers

What is claimed is:

1. A method for detecting the amplification of DNA and/or RNA sequences comprising:
   a) providing a sample containing at least a DNA or an RNA sequence amplification reaction mixture;
   b) inputting light into said sample;
   c) detecting a scattered light intensity produced by said sample with a detector;
   d) treating said sample under conditions suitable for amplifying at least DNA or RNA sequences in order to produce such amplified at least DNA or RNA sequences;
   e) determining the amplification of DNA or RNA sequences in the sample from an increase of the scattered light intensity, scattered exclusively by DNA or RNA.

2. The method of claim 1, wherein the sample is excited by a source, which is a light source selected from the group consisting of a lamp, a laser and an LED.

3. The method of claim 1, wherein the sample contains impurities.

4. The method of claim 1, wherein the quantities of products and/or educts are determined for known initial or end concentrations of products and/or educts.

5. The method of claim 1, wherein the sample contains impurities of at least one of foreign DNA or RNA sequences.

* * * * *